United States Patent [19]

Huang et al.

[11] Patent Number: 5,309,411
[45] Date of Patent: May 3, 1994

[54] TRANSDUCER

[76] Inventors: Dehua Huang, 135 Elm St., Milford, N.H. 03055; M. A. Breazeale, 1035 Zilla Avent. Dr., Oxford, Miss. 38655

[21] Appl. No.: 986,716

[22] Filed: Dec. 8, 1992

[51] Int. Cl.$^5$ ............................................. H04R 17/00
[52] U.S. Cl. ..................... 367/140; 367/150; 367/151; 367/157; 310/325; 310/334; 310/335; 310/336
[58] Field of Search ............... 367/150, 151, 157, 140; 310/322, 323, 325, 327, 328, 334, 335, 336, 337

[56] References Cited

U.S. PATENT DOCUMENTS

| | | | |
|---|---|---|---|
| 4,296,349 | 10/1981 | Nakanishi et al. | 310/335 |
| 5,212,671 | 5/1993 | Fajii et al. | 367/151 |

OTHER PUBLICATIONS

Du et al., "The Ultrasonic Field of a Gaussian Transducer," J. Acoust. Soc. Am. 78 (6):2083–2086 (1985).
Aanonsen et al., "Distortion and Harmonic Generation in the Nearfielddl of a Finite Amplitude Sound Beam," J. Acoust. Soc. Am. 75 (3):749–768 (1984).
Du et al., "An Ultrasonic Gaussian Transducer With a Curved Back Electrode," J. Acoust., Soc. Am. 89 (3): 1443–1447 (1991).
Hsu et al., "Ultrasonic Beams with Bessel and Gaussian Profiles" Review of Progress in Quantiative Nondestructive Evaluation 9:799–806, Plenun Press, N.Y. (1990).
Martin et al., "A Simple Way to Eliminate Diffraction Lobes Emitted by Ultrasonic Transducers," J. Acoust. Soc. Am. 49:1668–1669 (1971).

*Primary Examiner*—J. Woodrow Eldred
*Attorney, Agent, or Firm*—Hamilton, Brook, Smith & Reynolds

[57] ABSTRACT

A transducer apparatus and method for generating sonic sound waves having a far field wavefront amplitude pattern in a Bessel or Gaussian distribution is disclosed. The transducer includes a piezoelectric element having uniformly poled dipoles formed therein. An unpoled backing body having the same dielecctric constant as the piezoelectric element contacts and is attached to the piezoelectric element. An indentation shaped to produce a beam amplitude distribution of a predetermined function is formed on the backing body.

23 Claims, 4 Drawing Sheets

TRANSDUCER

BACKGROUND OF THE INVENTION

Electromagnetic beams having a Gaussian function wavefront amplitude distribution are advantageous for many reasons. One reason is that Gaussian beams are easy to model analytically. Another reason is that a circular Gaussian wavefront is free of near-field nulls and far-field sidelobes. In particular, sonic or ultrasonic beams having a Gaussian wavefront amplitude distribution are desirable in underwater acoustics, medical ultrasonics, nondestructive evaluation, acoustical microscopy, and nonlinear acoustics. A precise Gaussian beam reduces the possibility of waves reaching objects or areas where the beam is not directed. For example, in the acoustical field, background noise is substantially eliminated due to the reduction of stray sound waves.

Electromagnetic beams having a Bessel function wavefront distribution share some of the advantages of a Gaussian distribution but differ in that waves having a Bessel function distribution have the property that they do not spread and retain a narrow beam width.

Current transducers for generating Gaussian and Bessel function ultrasonic beams produce ultrasonic waves at relatively high frequencies but are unable to produce low frequency Gaussian function sound waves below 2 Hz. Low frequency sound waves are useful in applications such as sonar. Additionally, existing Gaussian function transducers generate sound wave amplitutude distributions having sidelobes with noise levels above −30 dB. Sidelobes are undesirable in that sidelobe sound waves can create signals reflected from objects other than the target.

Accordingly, there is a continuing need for an ultrasonic transducer which can generate ultrasonic sound waves in a Gaussian function amplitude distribution with low noise levels. Additionally there is a need for this transducer to be capable of generating these sound waves at low frequencies.

SUMMARY OF THE INVENTION

The present invention provides an apparatus and method for generating sonic sound waves having a far field wavefront amplitude pattern or distribution in accordance with a predetermined beam function. The term "sonic" as used herein is meant to encompass the Infrasonic, (0–10 Hz) Sonic (10 Hz to 10 KHz) and Ultrasonic frequency ranges. The term "ultrasonic" covers the range from about 10 KHz to about 30 MHz. The transducer includes a piezoelectric element having uniformly poled dipoles formed therein. "Uniformly poled" means that the magnetic fields of the dipoles found in the piezoelectric element are all aligned in the same direction and one of the same polarity. The piezoelectric element has an external surface that extends in a plane. One planar surface of an unpoled backing element or body contacts and is attached to an internal surface of the piezoelectric element. The dielectric constant of the unpoled backing element is substantively the same as the dielectric constant of the piezoelectric element. A second surface of the backing element which is opposite and parallel to the first surface has an indentation or concave cavity formed therein. The indentation is shaped to produce a beam amplitude distribution of a predetermined function or pattern. A first conductive electrode is formed on the external surface of the piezoelectric element. A second conductive electrode is formed on the indentation in the backing element. Alternating electric power is coupled across the electrode to energize the transducer. The alternating energizing voltage across the piezoelectric element and backing element, induces the piezoelectric element to vibrate and produce sonic waves having a predetermined beam amplitude distribution or shape which is mainly predicated upon the shape of the indentation in the unpoled backing element.

The shape of the sound waves produced by the present invention can be in a Gaussian or Bessel distribution depending upon the shape of the indentation on the backing element. When generating a Gaussian pattern or distribution of sound waves, the shape of the indentation in the backing body is spherical. When generating a Bessel pattern of sound waves, a series of indentations are formed in the backing body. The resulting pattern of sound waves produced have sidelobes below −30 dB at low frequencies. Theoretically, there is no lower limit on the frequencies producible by the present invention but there are practical limits due to manufacturing limitations.

BRIEF DESCRIPTION OF THE DRAWINGS

The foregoing and other objects, features an advantageous of the invention will be apparent from the following more particular description of the preferred embodiment of the drawings in which like reference characters refer to the same parts throughout the different views. The drawings are not necessarily to scale, emphasis instead being placed upon the illustrating the principles of the invention.

DETAILED DESCRIPTION OF THE PREFERRED EMBODIMENT

Figure 1:
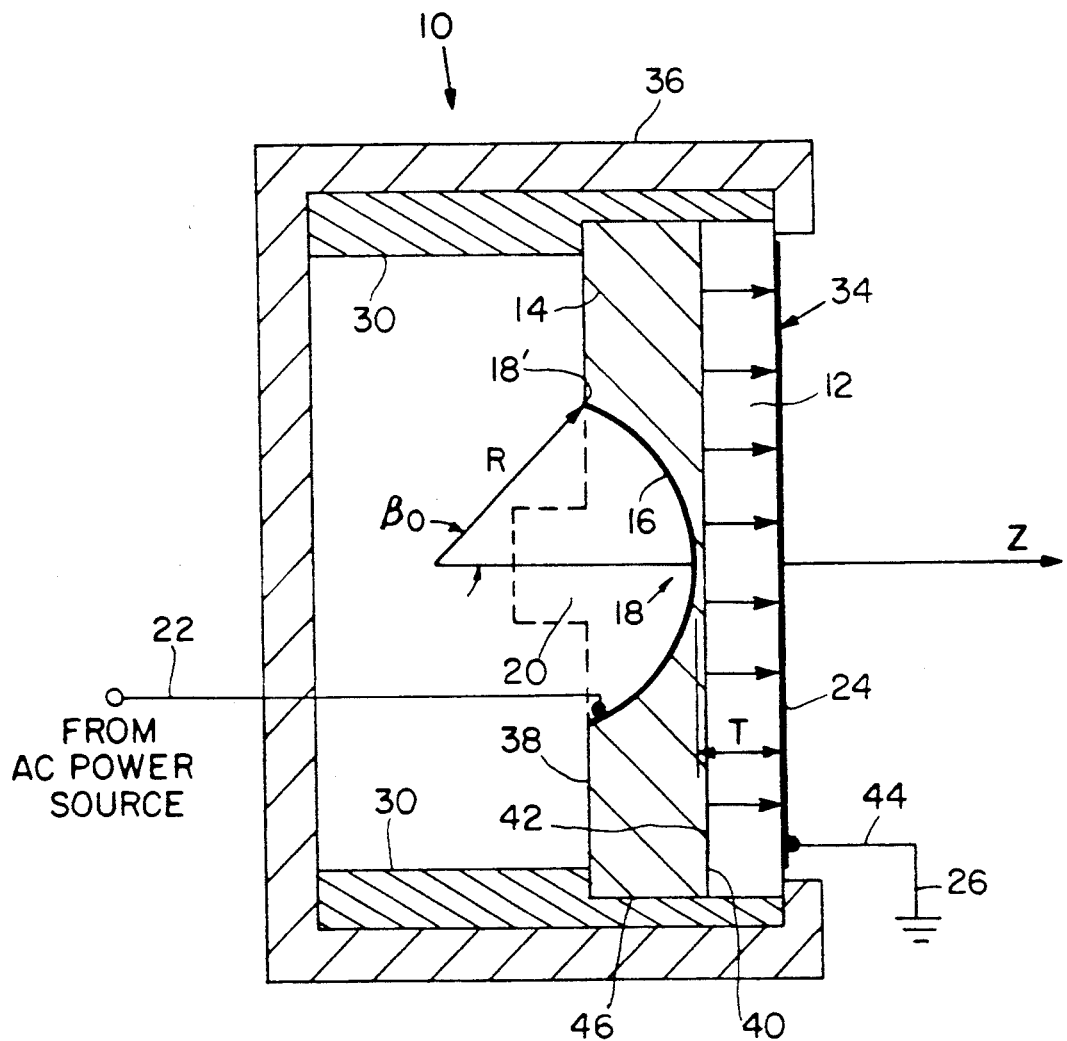
FIG. 1 is a schematic sectional view of an sonic Gaussian function transducer in accordance with the invention.

In FIG. 1 spherical button Gaussian transducer 10 has a piezoelectric plate 12 with an external surface 42 in contact with surface 40 of backing element 14. Fluid, usually water, is in contact with surface 24. Piezoelectric plate 12 is a ceramic piezoelectric disk in which the dipoles have been poled by subjecting the element to a high D.C. voltage which uniformly aligns the dipoles in the direction of the arrows. An electrode 34 is formed on surface 24. In the preferred embodiment electrode 34 is a silver coating formed on surface 24. Alternatively, surface 24 can be coated with other suitable conductive metals such as, gold, platinum etc. to form electrode 34. An electrical lead 44 connects electrode 34 to ground 26, thereby grounding piezoelectric plate 12.

Backing element 14 is preferably made from unpoled i.e., unmagnetized piezoelectric material having the same dielectric constant as piezoelectric plate 12. In the preferred embodiment, backing element 14 is made of the same material as piezoelectric plate 12 but can alternatively be made of any other suitable piezoelectric material that has the same dielectric constant as piezoelectric plate 12.

A spherical indentation 18 having a radius R is formed in surface 38 of backing element 14, such as by grinding or etching away material. Alternatively, spherical indentation 18 can be formed by other suitable processes such as by a molding process. In the preferred embodiment, spherical indentation 18 has an axial angle $\beta_0$ of about 43.6°. $\beta_0$ is the angle between the line drawn through the center of spherical indentation 18 perpendicular to the plane of plate 12 and a radius extending to one edge 18' of spherical indentation 18. Alternatively $\beta_0$ can be of other suitable angles close to 43.6°. In the preferred embodiment, the ratio between the radius R of spherical indentation 18 and minimum distance "T" between the two electrodes 16 and 34, (R/T) is about 3.73. R/T ratio of 3.73 provides the optimum distribution of sound waves for a Gaussian function and should be maintained regardless of the size of the transducer.

The spherical indentation 18 is coated with a conductive metal, which may also be silver, to form electrode 16. Alternatively, spherical indentation 18 can be coated with other suitable conductive metals, such as, gold, platinum, etc. Electrical lead 22 is connected to electrode 16 and provides electrical power across transducer 10 to ground. Alternatively, a brass electrode 20 (shown in dotted lines) can be disposed within spherical indentation 18 to serve as an electrode. In such a case, electrode 16 is not needed. In addition, electrode 20 can be made of other suitable conductive metals.

The piezoelectric plate 12 and backing element 14 are retained within bore 46 found in a retainer 30. Retainer 30 may be formed of a hollow electrically insulating tube formed of plexiglass or other suitable insulating material. Retainer 30 electrically isolates piezoelectric plate 12 and backing element 14 from housing 36. Housing 36 is made from metals, such as, aluminum or brass and provides environmental protection for piezoelectric plate 12 and backing element 14. Alternatively, housing 36 may be made of suitable high strength non-metallic materials. Housing 36 and retainer 30 form an airspace behind backing element 14.

An energizing A.C. voltage in the range of 100 volts to 1000 volts is generated across piezoelectric plate 12 and backing element 14 inducing piezoelectric plate 12 to vibrate and produce Gaussian shaped sound waves in the direction Z. Alternatively, lower or higher voltages can be used. The frequency of the sound waves generated depends on the size and thickness of piezoelectric plate 12. Smaller diameter transducers generate higher frequency sound waves while larger diameter transducers generate lower frequencies. Theoretically, there are no limits on the frequency range producible by the present invention. However, there are practical limits due to manufacturing limitations.

A theory as presently understood with respect to sound waves having a Gaussian amplitude distribution with transducer 10 is more fully discussed below although the invention is not to be limited to this theory.

Figure 2:
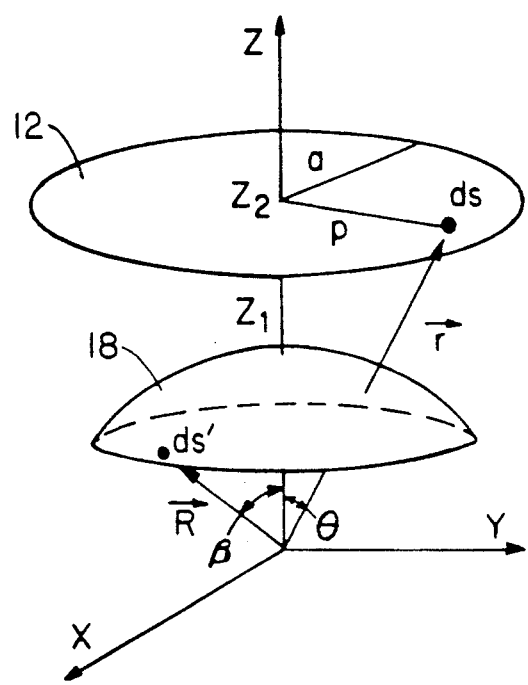
FIG. 2 is a schematic drawing showing the coordinates for calculating the electric field of a Gaussian transducer.

The configuration of ultrasonic Gaussian transducer 10 can be described by spherical coordinates as shown in FIG. 2, where: $Z_1 = R$ and $Z_2 = R + T$. Variable "all" is the radius of the piezoelectric disk 12, $\beta$ and $\Theta$ are axial angles with $0 \leq \beta \leq \beta_0$ and $0 \leq \theta \leq \theta_0$. Additionally, R is the radius of spherical indentation 18 (FIG. 1) and T is the minimum distance between electrodes 16 and 34. The plate 12 is assumed to be greater than the size of the spherical electrode 18 and the charge density $\sigma$ is assumed to be uniformly distributed on the surface of the spherical electrode 18 at time t. The electrode 34 (FIG. 1) in the plane $Z = Z_2$ is electrically grounded and is in contact with fluid (for example, water).

By using the image charge method, the electrical potential produced by the differential element ds' on ds is given by $$dv = \frac{dq}{|R\ r|} \tag{1}$$

where $dq = \sigma'(t)ds'$ and where $\sigma'(t)$ is the image charge density at time t on the surface ds'. R is the vector from the origin to ds' and r is the vector from the origin to ds. The element ds is in the plane $Z = Z_2$, where the Gaussian field distribution is desired.

For axial symmetry, the addition theorem for spherical harmonics allows one to write Eq. 1 in the form $$dv = 2\pi R^2 \sigma'(t) \sum_l P_l(\cos\theta) \tag{2}$$

$$\frac{R^l}{r^{l+1}} P_l(\cos\beta) \sin\beta \cdot d\beta$$

where $P_l(\cos\theta)$ is the lth order Lengender polynomial. Integrating Eq. 2 gives $$V = 2Q(t) \sum_l \frac{R^l}{r^{l+1}} P_l(\cos\theta) G_l(\beta_0) \tag{3}$$

where $$G_l(\beta_0) = \frac{1}{2l+1} [P_{l-1}(\cos\beta_0) - P_{l+1}(\cos\beta_0)]$$

and $Q(t) = \pi R^2 \sigma'(t)$ The z component of the electric field is $$E_z = -\nabla v.z. \tag{4}$$

On the surface of the plate where $Z = Z_2$, $$E_2 = 2Q(t) \sum_l \frac{R^l}{(T+R)^{l+2}} u^{l+2} G_l(\beta_0) \cdot \tag{5}$$

$$\left[ (l+1)u P_l(u) - (1-u^2) \frac{\partial P_l(u)}{\partial u} \right]$$

where $$u = \frac{1}{\left(1 + \left(\frac{P}{T+R}\right)^2\right)^{\frac{1}{2}}}$$

By controlling the ratio of R/T, where the thickness $T = Z_2 - Z_1$, and the axial angle $\beta_0$ for the spherical button, $E_z$ can approach a Gaussian distribution $E_z = E_{0z} e^{B\rho^2}$ with the Gaussian coefficient B needed.

A wave equation under a parabolic approximation, is given by $$\left( 4 \frac{\partial^2}{\partial \tau \partial \sigma} - \nabla_\perp^2 - 4a\tau_0 \frac{\partial^3}{\partial \tau^3} \right) P = 0 \tag{6}$$

where $\tau = \omega[t - (z/c_0)], P = p/\rho_0 c_0 u_0, \sigma = z/r_0$ and $r_0 = a^2\omega/2c_0$ are nondimensional variables. p, $c_0, \rho_0$ are sound pressure, sound velocity and static density of the medium. The distance z is measured in the direction of propagation of the sound wave, variable "a" is the radius of the transducer plate, $u_o$ is the characteristic velocity amplitude and $\alpha$ is the absorption coefficient of the medium. $\nabla^2_\perp$ denotes the nondimensional form of the transverse Laplacian operator. For the special case of a circular axisymmetric beam, we can substitute $\nabla^2_\perp = (1/\xi)(\partial/\partial\xi)[\xi(\partial/\partial\xi)]$ into Eq. (6), where $\xi = \rho/a$ and $\rho$ is the radial coordinate. The linearized solution for an axisymmetric source which oscillates sinusoidally in time is, in terms of nondimensional variables, $$p_1(\xi,\sigma,\tau) = \text{Re}[iq_1(\xi,\sigma)\exp(-i\tau - \alpha r_o \sigma 0)]. \tag{7}$$

where $$q_1(\xi,\sigma) = \frac{2}{i\sigma}\int_0^\infty \exp\left(i\frac{\xi^2 + \xi'^2}{\sigma}\right) J_0\left(\frac{2\xi\xi'}{\sigma}\right) q_1(\xi')\xi' d\xi'. \tag{8}$$

Thus one can express the diffraction problem in nondimentional variables, $\sigma = z/r_o$, the axial distance from the source, and $\xi = \rho/a$, the distance from the axis. At the source $\sigma = 0$, so the boundary condition becomes $$p(\xi,0,\tau) = q_1(\xi')\exp(-i\tau). \tag{9}$$

The Gaussian amplitude distribution at the source can be expressed in normalized form by letting $$q_1(\xi') = \exp(-B\xi'^2). \tag{10}$$

where we will refer to B as the Gaussian coefficient. Substituting Eq. (10) into Eq. (8), we get $$q_1(\xi,\sigma) = \tag{11}$$

$$\frac{2}{i\sigma}\int_0^\infty J_0\left(2\frac{\xi\xi'}{\sigma}\right)\exp\left[\left(\frac{i}{\sigma} - B\right)\xi'^2 + i\frac{\xi^2}{\sigma}\right]\xi' d\xi'.$$

which can be integrated directly to give $$q_1(\xi,\sigma) = \frac{1}{(1 + (B\sigma)^2)^{\frac{1}{2}}}\exp\left(-\frac{B}{1 + (B\sigma)^2}\right)\xi^2\exp(i\gamma). \tag{12}$$

where
$$\gamma = [B^2\sigma/(1+(B\sigma^0)^2)]\xi^2 - \tan^{-1}(B\sigma) + \pi/2$$

is a phase shift.

Inserting Eq. (12) into Eq. (7), one finds that the amplitude of the sound field produced by a transducer with a Gaussian velocity distribution is described by $$p_A(\xi,\sigma) = p_0 \frac{\exp(-\alpha r_0 \sigma)}{(1 + (B\sigma)^2)^{\frac{1}{2}}} \exp(-A\xi^2) \tag{13}$$

where $A = B/[1+(B\sigma)^2]$, is the Gaussian coefficient of the sound field $\xi = \rho/a$, $p_o$ is the sound pressure amplitude in the fluid at the center of the transducer.

Two important observations about the sound field can be made by noting the form of Eq. (13). First, as the wave propagates, the sound pressure on axis reduces gradually with distance $\sigma$. In the radiated beam, none of the maxima and minima typical of the Fresnel zone of a piston transducer appears. Second, the Gaussian coefficient of the sound field $A = B/(1+B^2\sigma^2)$ contains the source Gaussian coefficient B in a characteristic form and is a function of the distance $\sigma$ in the medium. This indicates that a transducer with a Gaussian amplitude distribution across its surface produces a sound field which is described by a Gaussian function both in the nearfield and the farfield. Furthermore, since the coefficient A gradually decreases with distance a from the source, the sound beam gradually spreads as it propagates, but does not develop the sidelobes characteristic of the farfield directivity pattern of a piston transducer.

Figure 3:
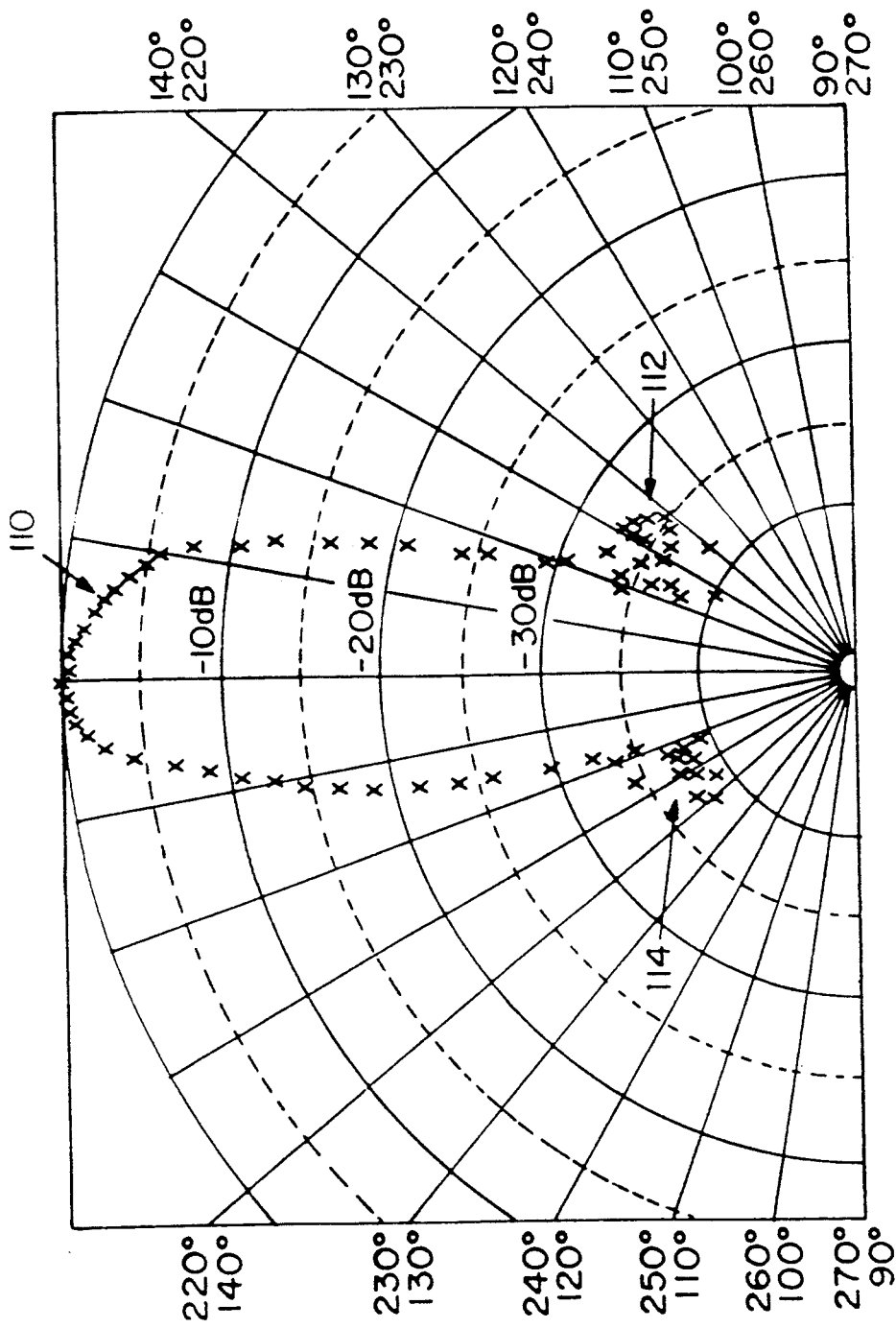
FIG. 3 is a graph of the beam pattern of a four inch spherical button Gaussian transducer at 375 KHz.

The amplitude distribution in sound waves generated by transducer 10 (FIG. 1) according to the theory discussed above are depicted in FIG. 3. The graph shows the Gaussian beam pattern 110 produced by a 4 inch spherical button Gaussian transducer at a frequency of 375 KHz. The sound waves of sidelobes 112 and 114 are 31 dB down as compared with the central beam.

Figure 4:
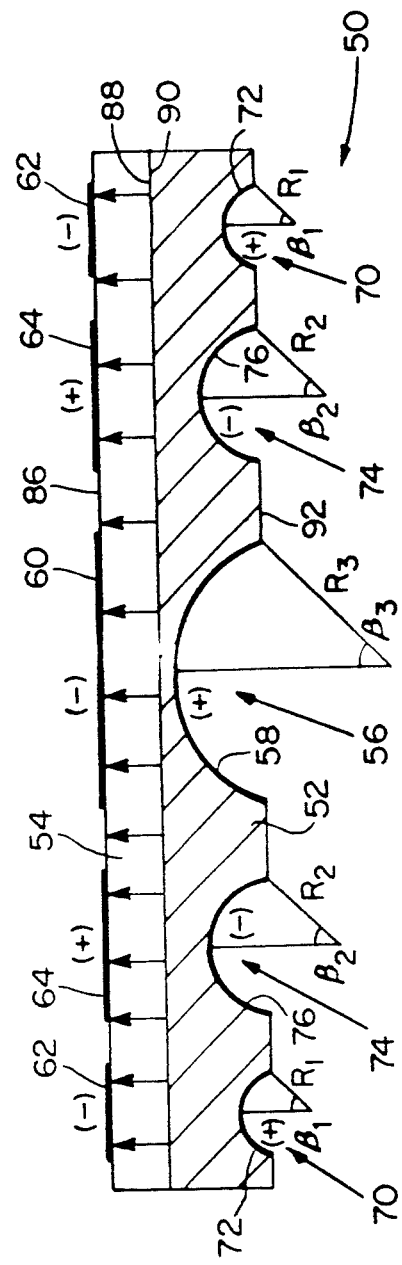
FIG. 4 is a schematic sectional view of a sonic Bessel function transducer in accordance with an alternate embodiment of the invention.

In FIG. 4, transducer 50 is another preferred embodiment of the present invention which generates sounds waves having a Bessel function amplitude distribution. Sound waves having in a Bessel function distribution do not spread.

Surface 88 of piezoelectric plate 54 is in contact with surface 90 of backing element 52. Piezoelectric plate 54 is a ceramic which is poled so that the dipoles are uniformly aligned in the direction of the arrows. A series of silver coatings on surface 86 form concentric circular electrodes 60, 62 and 64 on piezoelectric plate 54. Alternatively, surface 86 can be coated with other suitable conductive metals.

Backing element 52 is made of unpoled piezoelectric material having substantially the same dielectric constant as piezoelectric plate 54. Indentations 56, 70 and 74 are ground into surface 92 of backing element 52 by a grinder. The contours of indentations 56, 70 and 74 are shaped such that transducer 50 will generate a pattern of sound waves having a Bessel distribution. Alternatively, indentations 56, 70 and 74 can be formed by other suitable processes such as molding.

Indentation 74 encircles and is concentric about indentation 56. Indentation 70 encircles and is concentric about indentations 56 and 74. The radius $R_2$ 2 of indentation 74 is smaller than radius $R_3$ of indentation 56 and the radius $R_1$ is of indentation 70 is smaller than radius $R_2$ of indentation 74. In the preferred embodiment, three indentations are employed. However, in the alternative, the number of indentations employed can vary. Indentations 56, 74 and 70 are coated with silver to form electrodes 58, 76 and 72 and are located below electrodes 60, 64 and 62, respectively.

Figure 5:
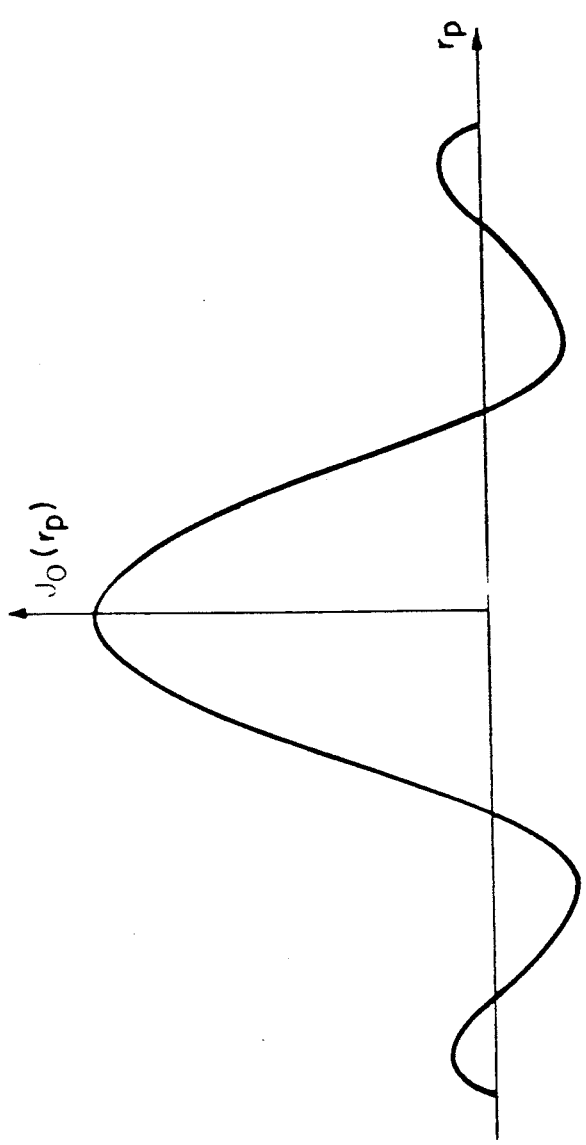
FIG. 5 is a graph of the beam distribution of a Bessel transducer.

Electrodes 60, 62 and 64 are connected to a ground by electrical leads (not shown) in a manner similar to that depicted in FIG. 1. Additionally electrodes 58, 76 and 72 are connected to electrical leads (not shown) which provide power to transducer 50. Electrical power is provided to transducer 50 in such a manner that electrode 58 is positively charged, electrode 76 is negatively charged, and electrode 72 is positively charged. corresponding electrodes 60, 64 and 62 are charged negatively, positively and negatively respectfully. These oppositely charged voltages across piezoelectric plate 54 and backing element 52 induce piezoelectric plate 54 to vibrate. generating sound waves having the Bessel distribution depicted in FIG. 5. The radius of piezoelectric plate 54 is designated by $r_p$ and $J_o$ designates the Bessel function of the sound waves generated.

While this invention has been particularly shown and described with references to preferred embodiments thereof, it will be under stood by those skilled in the art that various changes in form and details may be made therein without departing from the spirit and scope of the invention as defined by the appended claims.

We claim:

1. A transducer for generating sonic waves comprising:
   a piezoelectric element having dipoles formed therein, and an external surface extending in a plane;
   an unpoled backing element having a first surface contacting the piezoelectric element and a second surface opposite to the first surface having an indentation formed therein, the indentation shaped to produce a beam distribution of a predetermined function, the dielectric constant of the unpoled backing element being substantially the same as the dielectric constant of the piezoelectric element;
   a first electrode contacting the external surface of the piezoelectric element; and
   a second electrode contacting the indentation.

2. The transducer of claim 1 wherein the indentation is spherical in shape.

3. The transducer of claim 1 wherein the sonic waves generated have a Gaussian wavefront amplitude distribution.

4. The transducer of claim 1 further comprising a series of indentations formed in the first surface.

5. The transducer of claim 1 wherein the sound waves generated have a Bessel function amplitude distribution.

6. The transducer of claim 1 wherein the electrodes are formed by a silver coating on the external surface of the piezoelectric element and on the indentation.

7. The transducer of claim 1 wherein the sound waves generated are of low frequency.

8. The transducer of claim 7 wherein the low frequency sound waves generated are at frequencies below 2 MHz.

9. The transducer of claim 1 wherein the piezoelectric element is comprised of a ceramic.

10. The transducer of claim 1 wherein the dipoles of the piezoelectric element are uniformly poled.

11. A transducer for generating sound waves having a Gaussian function wavefront amplitude distribution comprising:
    a piezoelectric element having dipoles formed therein, and an external surface extending in a plane;
    an unpoled backing element having a first surface contacting the piezoelectric element and a second surface opposite to the first surface having a spherical indentation formed therein, the backing element having substantially the same dielectric constant as the dielectric constant of the piezoelectric element:
    a first electrode formed on the external surface of the piezoelectric element;
    a second electrode formed on the spherical indentation.

12. The transducer of claim 11 wherein the electrodes are formed by a silver coating on the external surface of the piezoelectric element and on the spherical indentation.

13. The transducer of claim 11 wherein the sound waves generated are of low frequency.

14. The transducer of claim 13 wherein the low frequency sound waves generated are at frequencies are below 2 MHz.

15. The transducer of claim 11 wherein the piezoelectric element is comprised of a ceramic.

16. The transducer of claim 11 wherein the dipoles of the piezoelectric element are uniformly poled.

17. A method for generating sound waves having a far field pattern shaped in accordance with a predetermined function comprising the steps of:
    a) providing a planar piezoelectric element having uniformally poled dipoles formed therein;
    b) attaching a planar backing body to the piezoelectric element in which the body has substantially the same dielectric constant as the piezoelectric element;
    c) shaping an indentation into the backing body, the shape of the indentation being in accordance with the desired pattern;
    d) generating an energizing voltage across the element and body to induce the element to vibrate and produce said shaped sound waves.

18. The method of claim 17 in which the sound waves produced are in a Gaussian function wavefront amplitude distribution.

19. The method of claim 17 in which the sound waves produced are in a Bessel function wavefront amplitude distribution.

20. The method of claim 17 in which the backing body is unpoled and the piezoelectric element is poled.

21. The method of claim 17 further comprising:
    forming a first electrical contact on the piezoelectric element; and
    forming a second electrical contact on the backing body.

22. The method of claim 17 in which the step of shaping comprises removing material from the backing body.

23. A method of generating sound waves comprising:
    vibrating a planar piezoelectric element having dipoles formed therein by applying a voltage across a piezoelectric element and a backing element, the backing element having a first surface contacting the piezoelectric element and a second surface opposite to the first surface which as an indentation shaped to produce sound waves having a distribution of a predetermined function, the dielectric constant of the backing element being substantially the same as the piezoelectric element.

* * * * *